(12) United States Patent
DiFoggio

(10) Patent No.: US 7,196,786 B2
(45) Date of Patent: Mar. 27, 2007

(54) METHOD AND APPARATUS FOR A TUNABLE DIODE LASER SPECTROMETER FOR ANALYSIS OF HYDROCARBON SAMPLES

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 10/836,675

(22) Filed: Apr. 30, 2004

(65) Prior Publication Data

US 2005/0007583 A1  Jan. 13, 2005

Related U.S. Application Data

(60) Provisional application No. 60/468,372, filed on May 6, 2003.

(51) Int. Cl.
G01J 3/44 (2006.01)
G01J 3/28 (2006.01)
G01V 5/08 (2006.01)

(52) U.S. Cl. .............. 356/301; 356/326; 250/269.1
(58) Field of Classification Search ...............
166/250.01–250.17, 251.1–255.3; 73/152.01–152.62;
250/253–268, 269.1, 269.2, 339.01–339.13,
250/340–342; 356/326, 319, 320, 301, 432,
356/436–442, 241.1–241.6
See application file for complete search history.

(56) References Cited

U.S. PATENT DOCUMENTS

| | | | |
|---|---|---|---|
| 2,813,980 A * | 11/1957 | De Witte | 250/260 |
| 3,994,592 A * | 11/1976 | Lardon et al. | 356/407 |
| 4,937,448 A | 6/1990 | Mantz et al. | |
| 5,317,156 A | 5/1994 | Cooper et al. | |
| 5,781,284 A | 7/1998 | Infante | |
| 6,023,340 A * | 2/2000 | Wu et al. | 356/432 |
| 6,064,488 A | 5/2000 | Brand et al. | |
| 6,353,225 B1 * | 3/2002 | Strzoda et al. | 250/339.13 |
| 6,437,326 B1 * | 8/2002 | Yamate et al. | 250/269.1 |
| 6,498,341 B2 * | 12/2002 | Dehnert et al. | 250/255 |
| 6,847,034 B2 * | 1/2005 | Shah et al. | 250/269.1 |
| 6,978,832 B2 * | 12/2005 | Gardner et al. | 166/250.1 |
| 2003/0033866 A1 | 2/2003 | Diakonov et al. | |
| 2003/0049858 A1 * | 3/2003 | Golden et al. | 436/171 |
| 2003/0134426 A1 | 7/2003 | Jiang et al. | |
| 2004/0164237 A1 | 8/2004 | Jones et al. | |
| 2004/0218176 A1 * | 11/2004 | Shammal et al. | 356/326 |

* cited by examiner

*Primary Examiner*—Gregory J. Toatley, Jr.
*Assistant Examiner*—Gordon J. Stock, Jr.
(74) *Attorney, Agent, or Firm*—Madan, Mossman & Sriram, P.C

(57) ABSTRACT

The present invention provides an down hole apparatus and method for ultrahigh resolution spectroscopy using a tunable diode laser (TDL) for analyzing a formation fluid sample downhole or at the surface to determine formation fluid parameters. In addition to absorption spectroscopy, the present invention can perform Raman spectroscopy on the fluid, by sweeping the wavelength of the TDL and detecting the Raman-scattered light using a narrow-band detector at a fixed wavelength. The spectrometer analyzes a pressurized well bore fluid sample that is collected downhole. The analysis is performed either downhole or at the surface onsite. Near infrared, mid-infrared and visible light analysis is also performed on the sample to provide an onsite surface or downhole analysis of sample properties and contamination level. The onsite and downhole analysis comprises determination of aromatics, olefins, saturates, gas oil ratio, API gravity and various other parameters which can be estimated by correlation, a trained neural network or a chemometric equation.

37 Claims, 7 Drawing Sheets

METHOD AND APPARATUS FOR A TUNABLE DIODE LASER SPECTROMETER FOR ANALYSIS OF HYDROCARBON SAMPLES

CROSS REFERENCE TO RELATED APPLICATIONS

This patent application claims priority from U.S. Provisional Patent Application Ser. No. 60/468,372 filed on May 6, 2003 entitled "A Method and Apparatus for a Tunable Diode Laser Spectrometer for Analysis of Hydrocarbon Samples," by Rocco DiFoggio.

BACKGROUND OF THE INVENTION

1. Field of the Invention

The present invention relates generally to the field of downhole sampling and in particular to the downhole and onsite surface ultrahigh resolution spectroscopy using a tunable diode laser for measurement and estimation of parameters of interest of hydrocarbon samples prior to, during, or after capture in a sample chamber.

2. Summary of the Related Art

Typically, sample tanks are transported to laboratories for analysis to determination formation fluid properties based on the sample. The samples have to be transferred to a transportation tank and, in so doing, risk sample damage and spoilage due to pressure loss and formation of bubbles or asphaltene precipitation in the sample. Moreover, even if the sample is transferred successfully, it typically takes weeks or months to receive the laboratory analysis. Thus, there is a need for a quicker sample analysis for downhole in situ analysis and for onsite surface analysis.

Currently spectral analysis downhole or onsite using optical filters is limited to around 11 nm full width half maximum wavelength resolution. These filters are not suitable to distinguish between close peaks, resolve small peaks superimposed on larger peaks, or to identity differences in isotopes whose features are much smaller than 11 nm. Thus, there is a need for an analysis technique suitable for downhole and onsite surface spectrographic analysis of hydrocarbon samples with high resolution on the order of 1–4 nm or much better. Manufacturers of tunable diode lasers often claim 0.01 nm or better resolution.

The present invention addresses the shortcomings of the related art described above. The present invention provides an apparatus and method for onsite surface and downhole spectral analysis of formation fluid samples, whether filtrate, hydrocarbon related or brine samples collected downhole in an earth boring or well bore. The present invention provides a tunable diode laser (TDL) for ultrahigh resolution spectroscopy (UHRS) and corresponding estimation of parameters of interest of such samples based on correlation to these UHRS measurements. A sorption cooling apparatus is also provided to cool the TDL and UHRS downhole if necessary. A plurality of TDLs are ganged together in one embodiment to span a hydrocarbon band of frequencies from approximately 1650 nm to 1850 nm or to provide a tunable spectral range over selected areas of interest in selected frequency bands. In an embodiment a TDL for UHRS is provided downhole for real time UHRS measurements and estimation of parameters of interest from the UHRS measurements. In another embodiment the TDL UHRS is performed at the surface onsite or by the UHRS in the tool or via a separate UHRS system attached at the surface. The TDL UHRS of the present invention is also useful for analysis of gases and fluids and isotopes thereof while flowing in distribution pipelines to determine the purity, grade and identity of hydrocarbon bearing fluids and gases.

BRIEF DESCRIPTION OF THE FIGURES

For detailed understanding of the present invention, references should be made to the following detailed description of the preferred embodiment, taken in conjunction with the accompanying drawings, in which like elements have been given like numerals, wherein.

DETAILED DESCRIPTION OF AN EXEMPLARY EMBODIMENT

Figure 1:
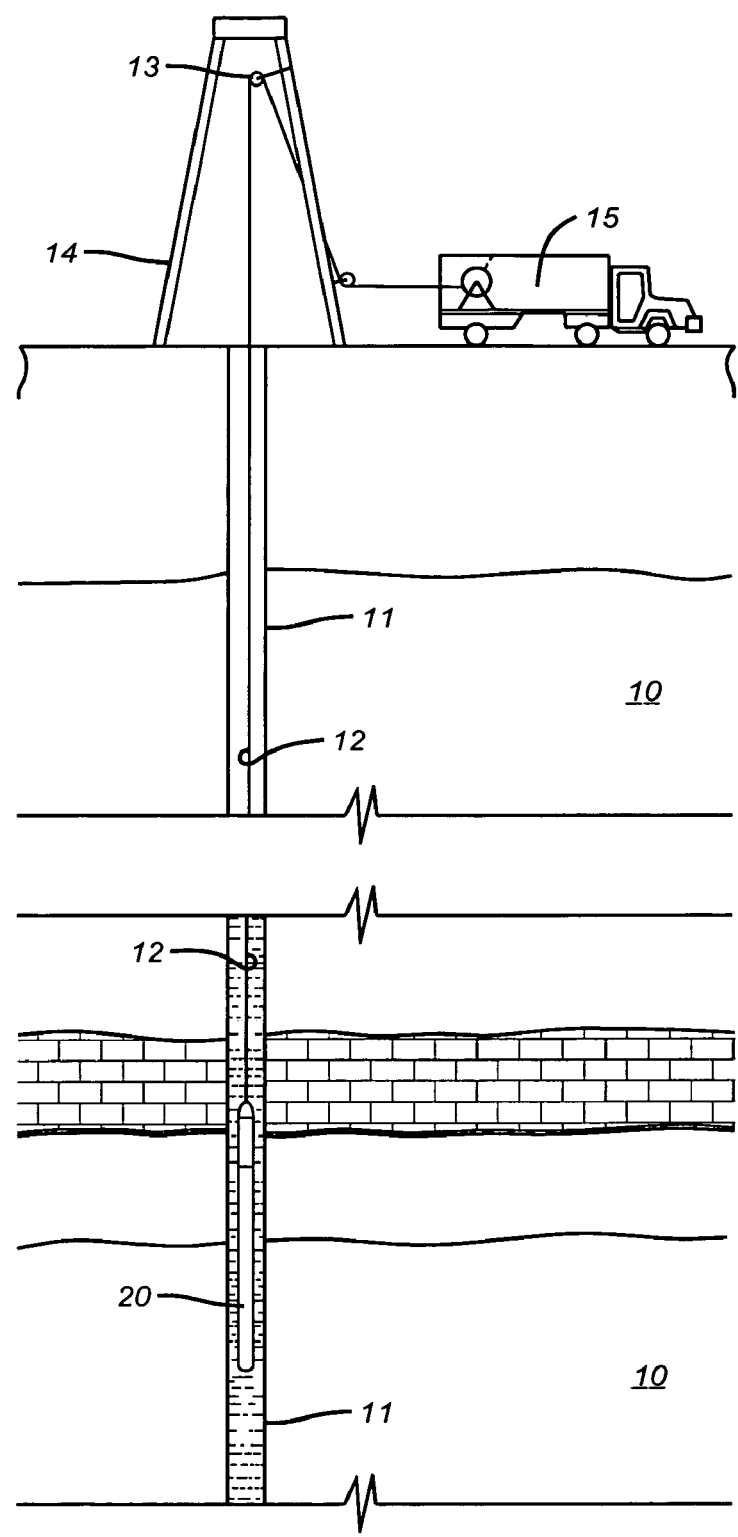
FIG. 1 is a schematic earth section illustrating the invention operating environment.

The present invention provides an ultrahigh resolution spectrometer using a tunable diode laser to enable high-resolution spectral measurements from which the present invention can estimate the percent of oil-based mud filtrate contamination in crude oil samples. The present invention also enables high-resolution spectral measurements to estimate the mole fraction or percent of chemical groups (aromatics, olefins, saturates) in a crude oil or gas sample or to measure gas oil ratio (GOR).

The present invention provides an ultrahigh resolution spectrometer using a tunable diode laser to enable high-resolution spectral measurements to estimate if a crude oil sample contains dry gas or wet gas (amounts of $C_1$ relative to amounts of $C_2$, $C_3$, and $C_4$). The present invention is also suitable for use in a pipeline, refinery or laboratories. The present invention provides an ultrahigh resolution spectrometer based on a tunable diode laser to enable spectral high-resolution measurements to estimate an amount of $CO_2$ in methane gas or $CO_2$ dissolved in a crude oil.

The present invention provides an ultrahigh resolution spectrometer using a tunable diode laser to enable high-resolution spectral measurements to provide improved correlations to physical properties (API Gravity, cloud point, bubble point, asphaltene precipitation pressure, etc.) or chemical properties (acid number, nickel, vanadium, sulfur, mercury, etc.) of crude oil or $^{13}C/^{12}C$ isotope ratios of methane gas.

The present invention provides an ultrahigh resolution spectrometer using a tunable diode laser to enable high-resolution spectral measurements to estimate the phytane/pristane ratios of crude oil.

The present invention provides a membrane to separate water vapor from liquid water for isotope analysis of the vapor. Examples of such membranes include Diaplex polyurethane membranes (available from Mitsubishi Heavy Industries) and Dermizax polyurethanes from available Toray Industries both of which are waterproof yet breathable for permeation by water vapor. The present invention also provides a membrane (such as a silicone rubber) to separate methane gas from liquid crude oil for gas isotope analysis of the gas. The present invention applies TDL spectroscopy to liquids and to gases dissolved in liquids.

The present invention provides an ultrahigh resolution spectrometer based on a tunable diode laser to enable high-resolution spectral measurement to estimate the $H_2S$ that is dissolved in crude oil. (NIR absorbance of 100% $H_2S$ is very weak, so the absorbance of 10 ppm of $H_2S$ is even weaker). The present invention provides an ultrahigh resolution spectrometer using a tunable diode laser to enable ultrahigh resolution spectral measurements to estimate the $^{17}O/^{18}O$ isotopes of water. The present invention provides an ultrahigh resolution spectrometer using a tunable diode laser to enable high-resolution spectral measurements to obtain approximate "synthetic" course-scale gas chromatograms (envelope of C1, C2, C3, etc.). The present invention provides an ultrahigh resolution spectrometer using a tunable diode laser to enable high-resolution spectral measurements to estimate the $^{13}C/^{12}C$ isotopes of methane gas.

The present invention provides a membrane to separate water vapor from liquid water for isotope analysis of the vapor. Examples of such membranes include Diaplex polyurethane membranes (Mitsubishi Heavy Industries) and Dermizax polyurethanes from Toray Industries both of which are waterproof yet breathable for permeation by water vapor. The present invention also provides a membrane (such as a silicone rubber) to separate methane gas from liquid crude oil for gas isotope analysis of the gas. The present invention applies TDL spectroscopy to liquids and to gases dissolved in liquids.

The present invention compensates for small wavelength range of TDLs by using several of these small lightweight sensors (TDLs) in selected wavelength regions. The present invention provides a high-temperature TDL spectrometer or cools an ordinary temperature (80° C.) TDL spectrometer with sorption cooling. The present invention provides a TDL to analyze the properties of a formation fluid sample in an optically transparent windowed sample tank. In one embodiment the present invention provides a set of wide-range (100–200 nm) ultra high resolution room-temperature or high temperature TDLs centered around the hydrocarbon band (1740 nm).

The present invention provides a high resolution TDL for spectral measurements from which to infer physical and chemical properties of sample formation fluids or other fluids not previously thought possible by spectroscopic means downhole or at the surface. The present invention takes advantage of the TDL's rapid wavelength switching capability to perform high resolution derivative spectroscopy, to for example, find peaks on a shoulder of another peak or to greatly improve signal to noise and makes it possible to observe subtle changes (e.g., 10–20 ppm $H_2S$), not possible with lower resolution conventional mid infrared (MIR) & near infrared (NIR) spectroscopy.

The present invention provides a two-pathlength (long and short path lengths) sample cell and a single photodetector so that the cell is self-referenced for absorbance or transmittance readings. The present invention provides a fast beam steering method (e.g., an acoustic-optic device or rotating prism, etc.) to shift the TDL beam between the thin (short path length) and thick (long path length) sections of the sample cell. Then, the optical absorbance for a pathlength that is equal to the difference between the long and short pathlengths is the base ten logarithm of the ratio of the short-path transmitted light intensity to the long-path transmitted light intensity.

The present invention provides a decompressible or evacuatable chamber covered by a membrane, which membrane is in contact with the liquid to extract vapor or gas to enable isotope analysis by the TDL spectrometer. The sample chamber flow path can be evacuated by withdrawing a piston to enlarge the chamber volume and lower the pressure within the chamber flow path drawing vapor through the membrane out of the liquid on the opposite side of the membrane.

Tunable diode lasers (TDLs) are provided for ultrahigh resolution spectroscopy (e.g., resolving $^{13}C$ methane gas from $^{12}C$ methane gas). U.S. Pat. No. 5,781,284, "System for detecting impurities contained in a fluid medium," describes using a tunable diode laser, but not for performing a spectral scan. The '284 patent teaches using a TDL to simply modulate a light at 400 Hz so as to distinguish the modulated signal from background. Intensity modulation of a light emitting diode could have served this purpose in U.S. Pat. No. 5,781,284 just as well instead of using a wavelength-modulated TDL.

The advantages of TDLs are their high intensity, extremely fine wavelength tunability, and comparatively small size and weight. Their disadvantages are the small tunable wavelength range over which they operate (4 to 10 nm is common, but increasingly TDLs are available with a tunable operating range of 100 nm or more) and their limited temperature range of operability (usually no more than 80° or 90° C.). Thus, the present invention provides a wide operating range TDL or an array of TDLs ganged together to cover a wide wavelength range of coverage and tuning within the range. Preferably, selected wavelength regions such as the hydrocarbon band, $CO_2$ band, $H_2S$ band, and the $H_2O$ band are selected for TDL spectral coverage and tuning within these bands. In a embodiment, the present invention spectrally separates isotopes of liquid water or isotopes of methane in a mixture of gases or when either is dissolved in liquid water or crude oil. A laboratory Fourier transform infrared (FTIR) spectrometer typically provides a 100 to 1000 times wider spectral range although an FTIR provides much lower light intensity at each wavelength and much less wavelength resolution. An FTIR laboratory spectrometer typically provides a wavelength resolution of 1 cm$^{-1}$ ("wave numbers") but TDLs can provide resolution as high as $10^{-4}$ cm$^{-1}$ or $10^{-5}$ cm$^{-1}$ providing ultra high resolution spectroscopy.

TDL spectroscopy is ideal for gas analysis because of its high resolution and ability to resolve the rotational splitting of the vibrational bands. The TDL is rapidly tuned when used for derivative spectroscopy. Thus, the TDL is useful to analyze for highly reactive systems such as free radicals, carbon clusters, ions, various reactive metal compounds, and weakly bound complexes.

Having a higher temperature (perhaps a quantum dot) TDL spectrometer fabricated or combining a tunable diode laser with downhole sorption cooling or other cooling mechanism overcomes temperature issues. For sorption cooling, the tunable diode laser is placed in thermal contact with a source of water (either liquid or as hydrate). The TDL is cooled as the water is evaporated from liquid or released by hydrate. The resulting water vapor is sorbed by a sorbent, which becomes hotter in the process. The sorbent transfers its excess heat to the well bore fluid with which it is in thermal contact through the tool housing.

The present invention quantifies aromatics, olefins (unlikely in crude oil but common in oil-based mud, OBM, filtrate), saturates, methane and quite possibly ethane, propane, and butane. With this high resolution spectroscopy, the present invention determines the percentage of oil based mud filtrate contamination downhole, particularly if the base oil is aromatic-free (unlike crude oil) but olefin-rich (also unlike crude oil).

Furthermore, with very high resolution, the present invention determines the isotopic ratios of methane ($^{13}C/^{12}C$) or isotopic ratios of water (for different oxygen isotopes) and quantifies gases such $CO_2$ (e.g., 1430 nm=6993 cm$^{-1}$, 1572 nm=6361 cm$^{-1}$, 1996 nm=5010 cm$^{-1}$, 2019 nm=4953 cm$^{-}$) or $H_2S$ (e.g. 1578 nm=6337 cm$^{31\ 1}$).

Alternatively, the present invention provides a set of sorption-cooled single-wavelength (not tunable) diode lasers, each at a carefully selected wavelength, to perform spectroscopy at a set of predetermined fixed wavelengths.

Tunable diode lasers (TDLS) are provided for very high resolution spectroscopy for gas and fluids at the surface and downhole. For example, TDLs are provided to quantify one gas in the presence of many others or to quantify different isotopes of the same gas. In one embodiment, by tuning the wavelength of the TDL light source and using a single-wavelength detector for any Raman-scattered light, the present invention also performs Raman spectroscopy.

One difficulty with implementing a tunable diode laser spectrometer downhole is temperature. Typically, manufacturers rate tunable diode lasers to temperatures of 80° C. or less. The inventor is aware of TDLs being operated up to about 100° C. but at that high of a temperature, TDLs produce far less light and may even become broadband light sources under higher temperature conditions.

The present invention combines a tunable diode laser with a downhole sorption cooling system, when necessary or desired, which cools the TDL spectrometer to enable operating the TDL at high ambient temperatures downhole while performing spectral measurements. The TDL is placed in thermal contact with a source of water (either as a liquid or as a hydrate). The TDL is cooled as water is evaporated from liquid or released by hydrate. The resulting water vapor which carriers heal away from the TDL and is sorbed by a sorbent, which becomes hotter in the process. The sorbent transfers its excess heat to the well bore fluid with which it is in thermal contact.

In an exemplary embodiment, a TDL is used to perform an ultrahigh resolution spectroscopy (UHRS) sweep of the hydrocarbon band from about 1650–1850 nm. Other frequency bands are swept as well depending on what elements or measurements are desired in measuring spectral transmissivity or absorbance. From these TDL spectral measurements, the present invention quantifies aromatics, olefins (unlikely in crude oil but common in OBM filtrate), saturates, methane and possibly ethane, propane, and butane. With this ultrahigh resolution TDL spectroscopy, referred herein as TDL UHRS, the present invention determines the percentage of oil based mud (OBM) filtrate contamination downhole, particularly if the OBM contaminants are aromatic-free but olefin-rich.

Figure 10:
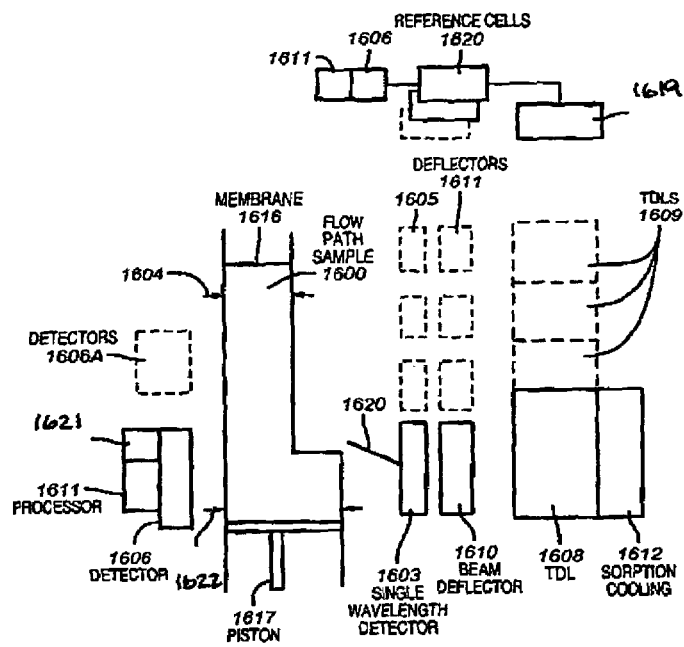
FIG. 10 is a schematic illustration of a preferred embodiment of a tunable diode laser spectrometer.

Furthermore, with ultrahigh resolution provided by the present invention, the present invention determines or estimates the isotopic ratios of methane ($^{13}C/^{12}C$) or isotopic ratios of water (for different oxygen isotopes) or quantify gases such $CO_2$ (e.g., 1430 nm, 1572 nm, 1996 nm, 2019 nm) or $H_2S$ (e.g. 1578 nm). As shown in FIG. 10, the present invention further comprises one or more reference cells 1620 containing known isotope gases for down hole reference to correct for temperature induced shifts of the spectra.

Alternatively, the present invention provides a set of single-wavelength (not tunable) diode lasers, each set at a carefully selected wavelength of interest, to perform spectroscopy at a set of predetermined fixed wavelengths. In another embodiment, a set of tunable TDLs are provided to measure over a set of wavelengths of interest corresponding to wavelengths associated with parameters of interest each TDL being tunable with a selected frequency band.

Turning now to FIG. 1, FIG. 1 schematically represents a cross-section of earth 10 along the length of a wellbore penetration 11. Usually, the wellbore will be at least partially filled with a mixture of liquids including water, drilling fluid, and formation fluids that are indigenous to the earth formations penetrated by the wellbore. Hereinafter, such fluid mixtures are referred to as "wellbore fluids". The term "formation fluid" hereinafter refers to a specific formation fluid exclusive of any substantial mixture or contamination by fluids not naturally present in the specific formation. Suspended within the wellbore 11 at the bottom end of a wire line 12 is a formation fluid sampling tool 20. The wire line 12 is often carried over a pulley 13 supported by a derrick 14. Wire line deployment and retrieval is performed by a powered winch carried by a service truck 15, for example.

Figure 2:
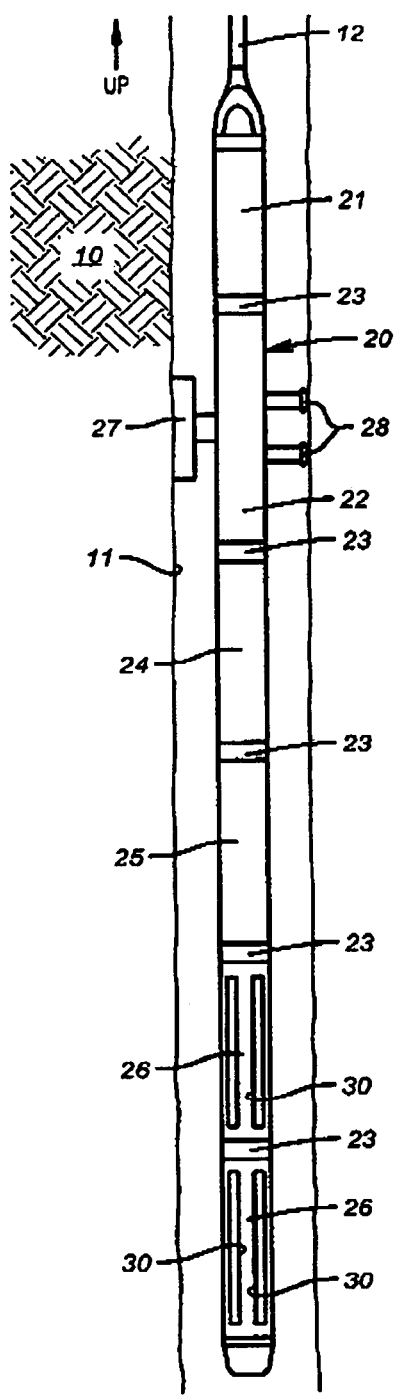
FIG. 2 is a schematic of the invention in operative assembly with cooperatively supporting tools.
Figure 3:
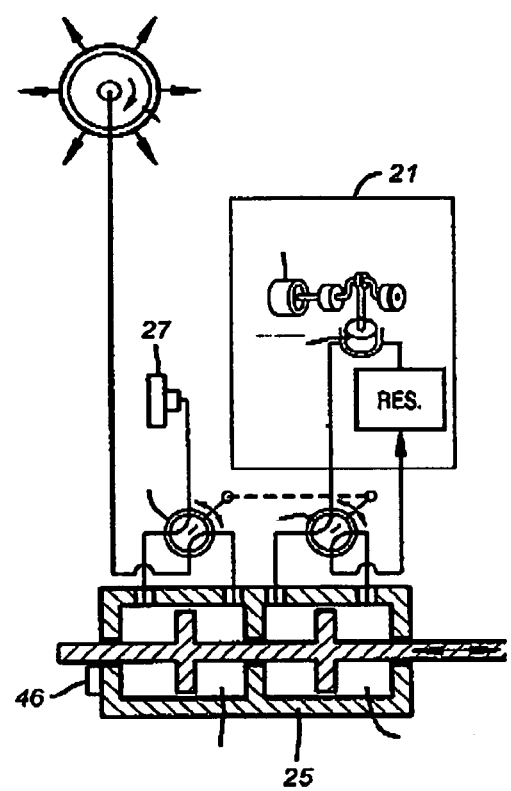
FIG. 3 is a schematic of a representative formation fluid extraction and delivery system.

Pursuant to the present invention, an exemplary embodiment of a sampling tool 20 is schematically illustrated by FIG. 2. Preferably, such sampling tools comprise an assembly of several tool segments that are joined end-to-end by the threaded sleeves or mutual compression unions 23. An assembly of tool segments appropriate for the present invention may include a hydraulic power unit 21 and a formation fluid extractor 23. Below the extractor 22, a large displacement volume motor/pump unit 24 is provided for line purging. Below the large volume pump is a similar motor/pump unit 25 having a smaller displacement volume that is quantitatively monitored as described more expansively with respect to FIG. 3. Ordinarily, one or more sample tank magazine sections 26 are assembled below the small volume pump. Each magazine section 26 may have three or more fluid sample tanks 30.

The formation fluid extractor 22 comprises an extensible suction probe 27 that is opposed by bore wall feet 28. Both, the suction probe 27 and the opposing feet 28 are hydraulically extensible to firmly engage the wellbore walls. Construction and operational details of the fluid extraction tool 22 are more expansively described by U.S. Pat. No. 5,303,775, the specification of which is incorporated herewith.

Figure 4:
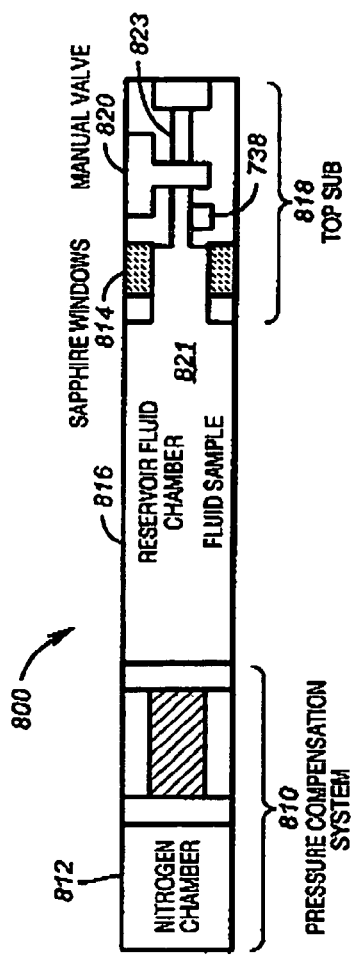
FIG. 4 is an illustration of a preferred sample chamber and analysis top sub.

Turning now to FIG. 4, in an embodiment of the present invention comprises an optically transparent windowed sample tank referred to herein as an advanced optical cylinder (AOC) 800 which further comprises a pressurized sample tank and analytical top sub 818, manual valve 820 and fluid path 823. The pressurized sample tank comprises a pressure compensation system 810, having a nitrogen pressure chamber 812 provided to apply high pressure on the fluid sample which is sufficient to keep a downhole captured fluid sample 821 in chamber 816 above the bubble point pressure and above the pressure at which asphaltenes precipitate out of the sample. The AOC is also suitable for downhole capture, pressurization and analysis of gas or fluid captured in chamber 816.

The AOC top sub 818 provides one or a pair of high pressure sapphire windows 814 TDL UHRS for optical analysis of parameters of interest for formation fluid sample 821. An analysis module 738 which embodies the TDL UHRS is provided for analysis of the sample downhole or at the surface.

Figure 5:
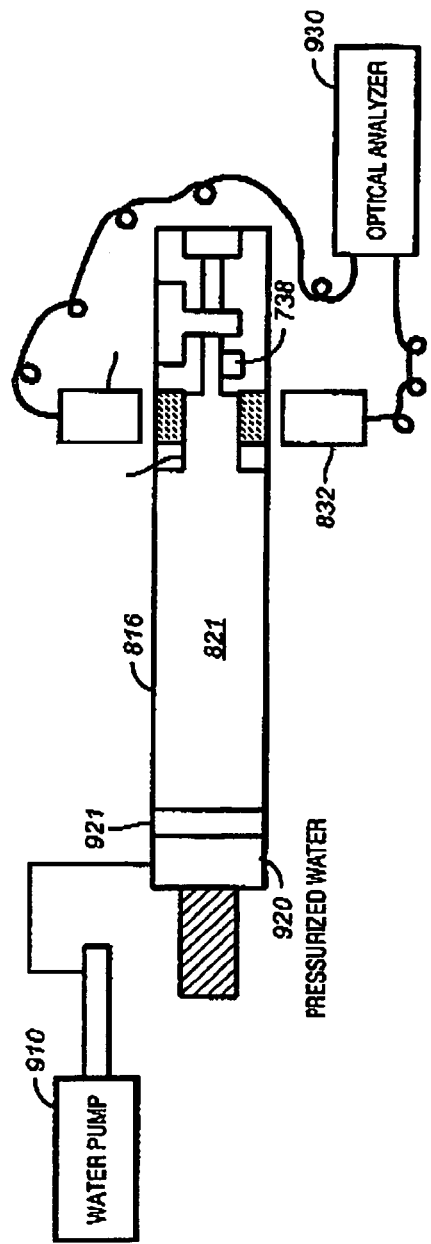
FIG. 5 is an illustration of an alternative embodiment having a water pump to pressurize a sample for analysis by an external unit.

In operation, as show in FIG. 5, the AOC is removed from a sample tank carrier and the sample 821 pressure is stabilized by pumping pressurized water 920 behind the piston 921 using pump 910. At this time nitrogen is released and the nitrogen chamber can be detected from the sample chamber. An external optical analyzer 930 or analysis module 738 comprising the TDL UHRS and preferably an NIR/MIR ultraviolet or visible light source and TDL spectrometers are provided for onsite analysis or downhole analysis. Such analysis can be performed without disturbing the fluid sample or requiring transferring the sample to another Department of Transportation (DOT) approved chamber for transport to an off-site laboratory for analysis. The optical analyzer of the present invention preferably uses wavelength ranges from approximately 1500 nm to 2000 nm to scan the fluid sample to determine sample contamination percentage, gas oil ratio (GOR), density and asphaltene deposition pressure. Low resolution conventional spectrometers, a tunable diode laser UHRS and TDL are operated in conjunction with a single-wavelength detector for Raman scattered light to perform Reman spectroscopy are also provided for spectral analysis of the fluid sample. One exemplary method for monitoring a parameter of interest for a down hole fluid sample utilizing the teachings of the present invention includes containing a fluid sample in a chamber downhole and spectrally analyzing the fluid sample with a tunable diode laser ultrahigh resolution spectrometer to determine a first parameter of interest for the fluid sample. In one variant, the method includes performing Raman spectroscopy by tuning the wavelength of light that enters the sample and measuring the Raman-shifted light using a single-wavelength detector. In another variant, the method includes shifting the wavelength of light from the TDL and analyzing the Raman spectra of fluid sample using a single-wavelength detector. In another variant, the method includes shifting a wavelength of light entering into the sample and detecting a single wavelength. In another variant, the method includes modulating the wavelength of the tunable diode laser for use as a derivative spectrometer. In another variant, the method includes sweeping the wavelength of light entering the sample while the Raman-shifted light at a single wavelength is detected. In another variant, the method includes modulating the wavelength of the tunable diode laser for use as a derivative spectrometer.

Figure 6:
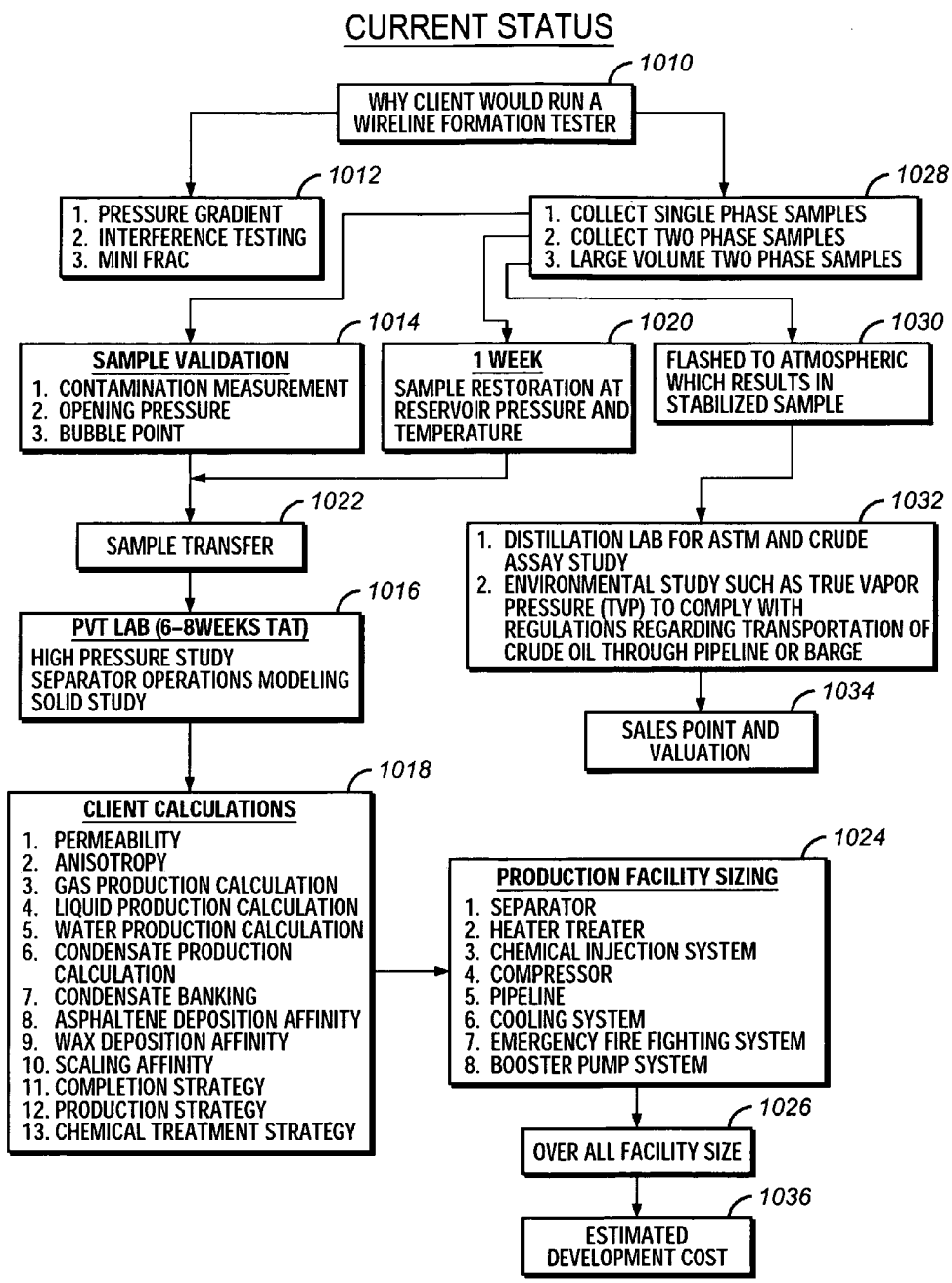
FIG. 6 is an illustration of a common current analysis procedure.
Figure 7:
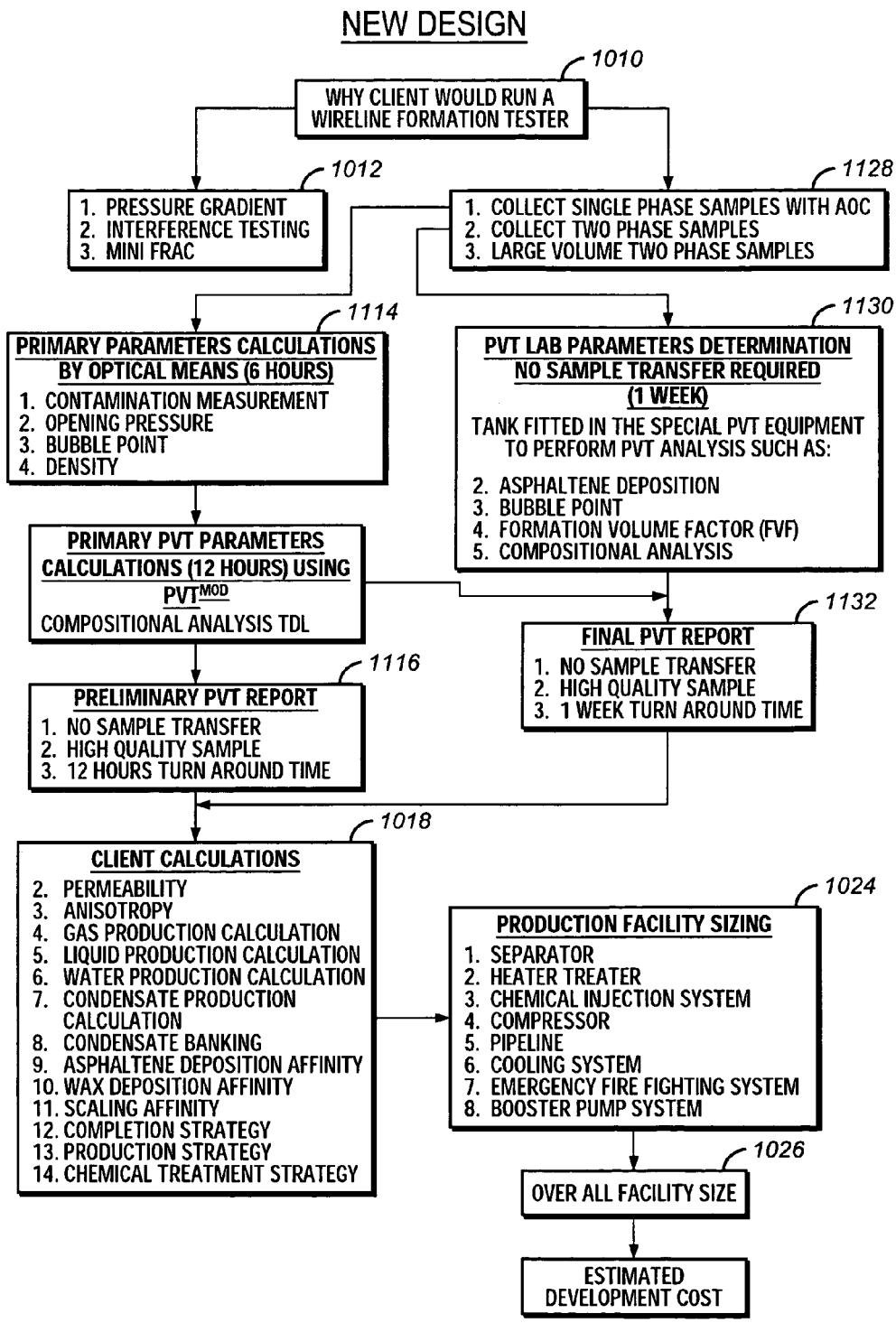
FIG. 7 is an illustration of the new improved procedure provided by the present invention.

The analysis module 738 embodying the preferred TDL UHRS and associated optical analysis equipment is attached or associated with in the AOC prior to going downhole. While downhole the TDL UHRS is used to perform analysis described herein during a downhole run or at the surface upon completion of a sampling run downhole. Some of the numerous advantages of the TDL UHRS of the present invention are shown by comparison of FIG. 6, 1010, 1012, 1014, 1022, 1016, 1018, 1028, 1030, 1034, 1024, 0126 and 1036 a commonly known system to which FIG. 7 illustrates the new design 1010, 1012, 1114, 1116, 1018, 1128, 1016, 1132, 1024 and provided by the TDL UHRS of the present invention. Note that in FIG. 7 that a Primary Parameter Calculation by an optical analysis system is available almost immediately in a relative sense or in less than six hours. A final PVT report is provided by the present invention in less than a week rather than six to eight weeks as shown in FIG. 6 for the common system. Moreover, there is no sample transfer required as onsite equipment in both the analysis module 738 and external equipment 830 perform PVT and spectral analysis to determine asphaltene deposition, bubble point, formation volume factor, compositional analysis and additional analysis described herein.

Figures 8, 9:
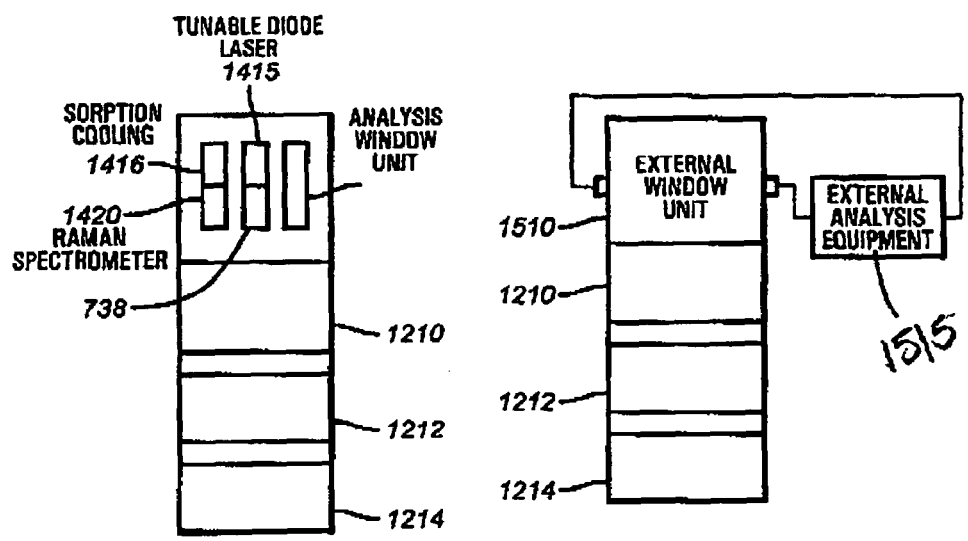
FIG. 8 is an illustration of an alternative embodiment.
FIG. 9 is an illustration of another alternative embodiment.

Turning now to FIG. 8 an alternative embodiment of the present invention is presented showing top sub 818 containing analysis module 738 attached to sample chamber 1210 pressurized by nitrogen (N2) 1212 and hydrostatic pressure 1214 while downhole. Thus, the present invention performs sampling and TDL UHRS sample analysis while downhole or at the surface.

As shown in FIG. 8, the analysis window unit comprises an analysis module 738, a tunable diode laser spectrometer 1415, additional Raman Spectrometer 1420 and a sorption cooling unit 1416. Sorption cooling unit 1416 is described in co-owned patent application Ser. No. 09/756,764 filed on Jan. 8, 2001 entitled "Downhole Sorption Cooling in Wireline Logging and Monitoring While Drilling" by Rocco DiFoggio, incorporated herein by reference in its entirety. As shown in FIG. 9, an external TDL UHRS 1515 is attached to the AOC to analyze the sample at the surface via external window unit 1510.

The preferred tunable diode laser 1415 spectrometer enables the present invention to perform ultrahigh resolution spectroscopy downhole during or prior to sampling, after sampling or at the surface. Sorption cooling unit 1416 cools is provided if needed adjacent the tunable diode laser and other electronics downhole as necessary to obviate the adverse affects of downhole temperatures.

Turning now to FIG. 10 a preferred embodiment of the present invention is shown. In a preferred embodiment, a TDL 1608 or multiple TDLs 1609 are provided along with a spectral detector 1606 or multiple spectral detectors 1606a. A processor is provided for controlling the TDL, controlling all electronics such as the color shifter 1603, and for reading sampling or measuring detector 1606. The processor also controls beam deflector 1610 to deflect a beam from TDL between the short sample flow path 1604 and the long sample flow path 1602 to determine the ratio between thy two paths. A single-wavelength detector(s) 1603, 1605 is (are) provided to perform Raman spectroscopy of the fluid and to enable detection of nitrogen and other infrared inactive components in a gas or liquid sample. A reference cell 1620 is also provided.

The additional TDLs 1609, 1619 are selected at wavelengths of interest to analyze the sample for peaks relating to a measurable spectral component or to estimate a parameter of interest from the selected measured components. A soft modeling technique such as, but not limited to, a trained neural network or chemometric equation resident in the processor 1611 and developed based on a correlation between parameters of interest and measured spectral content is used to estimate parameters of interest (GOR, API gravity, etc.) for the fluid or gas sample for which the TDL is used to measure spectral content Membrane 1616 is optionally provided to separate liquid from vapor in the sample flow path when desired. Piston 1617 is provided to evacuate the sample flow path 1600 to pull vapor into the sample flow path past the membrane 1616 for analysis of gas only in the flow path.

Figure 11:
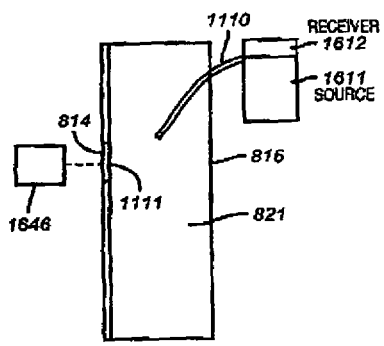
FIG. 11 is an example of an alternative embodiment for determining reflectance spectra using a tunable diode laser attached to an optical probe.

Turning now to FIG. 11, in an alternative example of the invention, tunable diode laser spectrometer probe 1110 is inserted into the sample 821 to transmit from TDL source 1611 and to receive returned light using receiver 1612 to determine optical characteristics forte sample 821. TDL source and receiver 1646 transmits light through optical window 814 to the interface 1111 between the sample 821 and the window 814 to measure light reflected off of the liquid window interface 1111 to determine reflectance spectra of the sample.

In another embodiment, the method of the present invention is implemented as a set computer executable of instructions on a computer readable medium, comprising ROM, RAM, CD ROM, Flash or any other computer readable medium, now known or unknown that when executed cause a computer to implement the method of the present invention.

While the foregoing disclosure is directed to the preferred embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

The invention claimed is:

1. A downhole apparatus for monitoring a parameter of interest for a fluid sample downhole comprising:
   a downhole tool containing a chamber for containing a fluid sample downhole; and
   a cooled downhole tunable diode laser spectrometer for analyzing the fluid sample to determine a first parameter of interest for the fluid sample.

2. The apparatus of claim 1, wherein the tunable diode laser spectrometer further comprises a plurality of tunable diode lasers for analyzing a band of frequencies associated with the fluid sample.

3. The apparatus of claim 1, wherein the tunable diode laser spectrometer further comprises a single-wavelength detector Raman spectrometer for analyzing the fluid sample.

4. The apparatus of claim 1, wherein the spectrometer further comprises a processor configured to use a neural network, chemometric equation or least mean squares fit for estimating a parameter of interest from the tunable diode laser spectrometer measurements.

5. The apparatus of claim 1, wherein the tunable diode laser spectrometer uses derivative spectroscopy.

6. The apparatus of claim 1, further comprising:
   a neural network for estimating a second parameter of interest for the fluid sample from the first parameter of interest of the fluid sample.

7. The apparatus of claim 1, further comprising:
   a chemometric equation for estimating a second parameter of interest for the fluid sample from the first parameter of interest for the fluid sample.

8. The apparatus of claim 1, wherein the tunable diode laser spectrometer performs measurements over a hydrocarbon band of frequencies, substantially from 1650–1850 nm.

9. The apparatus of claim 1, further comprising a sorption cooling unit cooling the tunable diode laser spectrometer.

10. The apparatus of claim 9, wherein the sorption cooling unit includes a liquid that absorbs heat generated by the tunable diode laser spectrometer.

11. A downhole apparatus for monitoring a parameter of interest for a fluid sample comprising:
   a downhole tool containing a chamber for containing a fluid sample downhole;
   a cooled tunable diode laser spectrometer for analyzing the fluid sample to determine a first parameter of interest for the fluid sample; and
   a membrane for separating vapor from liquid for isotope analysis of vapor.

12. A downhole apparatus for monitoring a parameter of interest for a fluid sample downhole comprising:
   a downhole tool containing a chamber for containing a fluid sample downhole; and
   a cooled downhole tunable diode laser spectrometer for analyzing the fluid sample to determine a first parameter of interest for the fluid sample, wherein the tunable diode laser spectrometer further comprises a single-wavelength detector Raman spectrometer for analyzing the fluid sample, wherein Raman spectroscopy is performed by tuning a wavelength of light that enters the fluid sample and measuring the Raman-shifted light using the single-wavelength detector.

13. A method for monitoring a parameter of interest for a fluid sample downhole comprising:
   containing a fluid sample in a chamber downhole; and
   spectrally analyzing the fluid sample downhole with a cooled downhole tunable diode laser spectrometer to determine a first parameter of interest for the fluid sample.

14. The method of claim 13, further comprising:
   analyzing a band of spectral frequencies of the fluid sample.

15. The method of claim 13, further comprising: estimating a parameter of interest from the tunable diode laser measurements using a soft modeling technique, selected from one of a neural network, a chemometric equation and a least mean square fit.

16. The method of claim 13, wherein a wavelength of the tunable diode laser spectrometer is modulated for use as a derivative spectrometer.

17. The method of claim 13, further comprising:
   estimating a second parameter of interest for the fluid sample from the first parameter of interest of the fluid sample using a neural network.

18. The method of claim 13, further comprising:
   estimating a second parameter of interest for the fluid sample from the first parameter of interest for the fluid sample using a chemometric equation.

19. The method of claim 13, further comprising: spectrally analyzing the fluid sample by performing tunable diode spectral measurements over a hydrocarbon band of frequencies, substantially in a range from 1650–1850 nm.

20. The method of claim 13, further comprising cooling the tunable diode laser spectrometer using sorption cooling.

21. The method of claim 20, wherein sorption cooling is performed using a liquid.

22. A method for monitoring a parameter of interest for a fluid sample downhole comprising:
   containing a fluid sample in a chamber downhole; and
   spectrally analyzing the fluid sample downhole with a cooled downhole tunable diode laser spectrometer to determine a first parameter of interest for the fluid sample; and
   separating vapor from the fluid sample through a membrane for analysis of the vapor.

23. A method for monitoring a parameter of interest for a fluid sample downhole comprising:
   containing a fluid sample in a chamber downhole; and
   spectrally analyzing the fluid sample downhole with a cooled downhole tunable diode laser spectrometer to determine a first parameter of interest for the fluid sample; and shifting a wavelength of light from the tunable diode laser spectrometer; and analyzing Raman spectra of fluid sample using a single-wavelength detector Raman spectrometer.

24. A method for monitoring a parameter of interest for a fluid sample downhole comprising:

containing a fluid sample in a chamber downhole; and spectrally analyzing the fluid sample downhole with a cooled downhole tunable diode laser spectrometer to determine a first parameter of interest for the fluid sample wherein a wavelength of light entering into the sample is shifted and a single wavelength is detected.

25. A computer readable medium containing computer instructions that when executed by a computer perform a method for monitoring a parameter of interest for a fluid sample downhole comprising:

spectrally analyzing a fluid sample contained in a chamber downhole with a cooled tunable diode laser ultra-high resolution spectrometer to determine a first parameter of interest for the fluid sample.

26. The medium of claim 25, wherein the method further comprises: analyzing the fluid sample over a band of spectral frequencies.

27. The medium of claim 25, wherein the method further comprises: estimating a parameter of interest from the tunable diode laser measurements using a soft modeling technique, selected from one of a neural network, a chemometric equation, and a least means square fit.

28. The medium of claim 25, wherein a wavelength of the tunable diode laser spectrometer is frequency-modulated for use as a derivative spectrometer.

29. The medium of claim 25, wherein the method further comprises:

estimating a second parameter of interest for the fluid sample from the first parameter of interest of the fluid sample using a neural network.

30. The medium of claim 25, wherein the method further comprises:

estimating a second parameter of interest for the fluid sample from the first parameter of interest for the fluid sample using a chemometric equation.

31. The medium of claim 25, wherein the method further comprises: spectrally analyzing the fluid sample by performing tunable diode spectral measurements over a hydrocarbon band of frequencies, substantially from 1650–1850 nm.

32. The medium of claim 25, wherein the cooled tunable diode spectrometer is cooled using sorption cooling.

33. The medium of claim 32, wherein the sorption cooling is performed using a liquid.

34. A computer readable medium containing computer instructions that when executed by a computer perform a method for monitoring a parameter of interest for a fluid sample downhole comprising:

spectrally analyzing a fluid sample contained in a chamber downhole with a cooled tunable diode laser ultra-high resolution spectrometer to determine a first parameter of interest for the fluid sample; and spectrally analyzing a vapor separated from the fluid sample.

35. A computer readable medium containing computer instructions that when executed by a computer perform a method for monitoring a parameter of interest for a fluid sample downhole comprising:

spectrally analyzing a fluid sample contained in a chamber downhole with a cooled tunable diode laser spectrometer to determine a first parameter of interest for the fluid sample; shifting a wavelength of light from the tunable diode laser spectrometer; and analyzing a Raman spectra of the fluid sample using a single-wavelength detector Raman spectrometer.

36. A computer readable medium containing computer instructions that when executed by a computer perform a method for monitoring a parameter of interest for a fluid sample downhole comprising:

spectrally analyzing a fluid sample contained in a chamber downhole with a cooled tunable diode laser spectrometer to determine a first parameter of interest for the fluid sample; wherein a wavelength of light entering the sample is swept while a Raman-shifted light at a single wavelength is detected.

37. A system for monitoring a parameter of interest for a fluid sample downhole comprising:

a surface controller for deploying a downhole tool;

a chamber in the downhole tool containing a fluid sample downhole; and a cooled tunable diode laser spectrometer downhole for analyzing the fluid sample downhole to determine a parameter of interest for the fluid sample downhole.

* * * * *